US011480483B2

(12) United States Patent
Tanaka

(10) Patent No.: US 11,480,483 B2
(45) Date of Patent: Oct. 25, 2022

(54) LOAD DETECTOR, METHOD FOR MANUFACTURING SAME, AND LOAD DETECTING SYSTEM

(71) Applicant: MINEBEA MITSUMI INC., Nagano (JP)

(72) Inventor: Manabu Tanaka, Fujisawa (JP)

(73) Assignee: MINEBEA MITSUMI Inc., Nagano (JP)

( * ) Notice: Subject to any disclaimer, the term of this patent is extended or adjusted under 35 U.S.C. 154(b) by 0 days.

(21) Appl. No.: 17/055,667

(22) PCT Filed: May 10, 2019

(86) PCT No.: PCT/JP2019/018698
§ 371 (c)(1),
(2) Date: Nov. 16, 2020

(87) PCT Pub. No.: WO2019/221018
PCT Pub. Date: Nov. 21, 2019

(65) Prior Publication Data
US 2021/0239547 A1    Aug. 5, 2021

(30) Foreign Application Priority Data
May 17, 2018    (JP) .............................. JP2018-095133

(51) Int. Cl.
*G01L 1/22*    (2006.01)
*A61B 5/00*    (2006.01)
(Continued)

(52) U.S. Cl.
CPC .............. *G01L 1/22* (2013.01); *A61B 5/6891* (2013.01); *G01G 19/52* (2013.01); *G01G 21/22* (2013.01)

(58) Field of Classification Search
CPC .......... G01L 1/22; G01G 19/52; G01G 21/22; G01G 3/14; G01G 19/02; G01G 19/021;
(Continued)

(56) References Cited

U.S. PATENT DOCUMENTS 2,962,276 A * 11/1960 Thurston ................ G01G 19/00
177/126
3,191,701 A *  6/1965 Gray .................... G01G 19/025
177/209

(Continued)

FOREIGN PATENT DOCUMENTS

CN         1129978 A      8/1996
CN         2539155 Y  *   3/2003
(Continued)

OTHER PUBLICATIONS

English translation of the Written Opinion for corresponding International Application No. PCT/JP2019/018698 dated Jun. 11, 2019.
(Continued)

Primary Examiner — Marrit Eyassu
(74) Attorney, Agent, or Firm — Pearne & Gordon LLP

(57) ABSTRACT

A load detector for detecting a load of a subject on a bed (BD) having a caster (CT) includes: a plate portion (1) which is one-fold and which is to be supported above an installation surface (F), on which the load detector is installed, separately from the installation surface; and a slope portion (SL1, SL2, SL3, SL4) which is provided around the plate portion and which is inclined relative to a surface of the plate portion so as to extend between the surface of the plate portion and the installation surface. The plate portion includes: a peripheral part (13); a placing part (11) on which the caster is to be placed, and which is provided inside relative to the peripheral part separately from the peripheral part; and a linking part (12) which links the placing part and the peripheral part. The load detector further includes a
(Continued)

strain sensor (G) attached to the linking part, and the slope portion includes at least two pairs of slopes (SL1, SL2, SL3, SL4) each including a pair of slopes opposed to each other such that the placing part is interposed between the pair of slopes.

15 Claims, 11 Drawing Sheets

(51) Int. Cl.
*G01G 21/22* (2006.01)
*G01G 19/52* (2006.01)

(58) Field of Classification Search
CPC .... G01G 19/025; G01G 19/027; G01G 19/44; G01G 19/445; G01G 21/18; G01G 21/24; A61B 5/6891
USPC .......................................................... 338/2
See application file for complete search history.

(56) References Cited

U.S. PATENT DOCUMENTS

| | | | |
|---|---|---|---|
| 3,935,913 A * | 2/1976 | Wagner | G01G 21/22 |
| | | | 177/134 |
| 4,775,018 A | 10/1988 | Kroll et al. | |
| 5,086,856 A * | 2/1992 | Haggstrom | G01G 19/445 |
| | | | 177/1 |
| 5,786,549 A | 7/1998 | Serizawa | |
| 7,381,910 B1 * | 6/2008 | Wilkerson | G01G 19/445 |
| | | | 177/144 |
| 9,506,106 B2 | 11/2016 | Gough et al. | |
| 10,365,149 B2 | 7/2019 | Gough et al. | |
| 2008/0217072 A1 * | 9/2008 | Domel | G01G 19/44 |
| | | | 177/145 |
| 2009/0051549 A1 * | 2/2009 | Tochigi | G01G 19/445 |
| | | | 340/573.4 |
| 2015/0101870 A1 | 4/2015 | Gough et al. | |
| 2017/0067774 A1 | 3/2017 | Gough et al. | |

FOREIGN PATENT DOCUMENTS

| | | | | |
|---|---|---|---|---|
| CN | 2539155 | Y | 3/2003 | |
| CN | 103267610 | A | 8/2013 | |
| DE | 1549309 | A1 | 4/1971 | |
| JP | 11-223546 | A | 8/1999 | |
| JP | 2008-065700 | A | 3/2008 | |
| JP | 2012-088323 | A | 5/2012 | |
| JP | 5143946 | B2 | 2/2013 | |
| JP | 2017-194393 | A | 10/2017 | |
| WO | WO-9525262 | A1 * | 9/1995 | ............. G01G 21/16 |
| WO | 2007/066638 | A1 | 6/2007 | |

OTHER PUBLICATIONS

Notification of the First Office Action for Chinese Application No. 201980032649 2 with translation dated Feb. 26, 2021.
International Search Report for corresponding International Application No. PCT/JP2019/018698 dated Jun. 11, 2019.
Written Opinion for corresponding International Application No. PCT/JP2019/018698 dated Jun. 11, 2019.
Decision to Grant a Patent for corresponding Japanese Application No. 2018-095133 dated Jan. 21, 2020 and English translation.
Decision of Rejection dated Jan. 12, 2022 for corresponding Chinese Application No. 201980032649.2 and English translation.
Extended European Search Report dated Feb. 9, 2022 for European Patent Application No. 19802962.1.
Chinese Office Action dated Oct. 11, 2021 for corresponding Chinese Application No. 201980032649.2 and English translation.

* cited by examiner

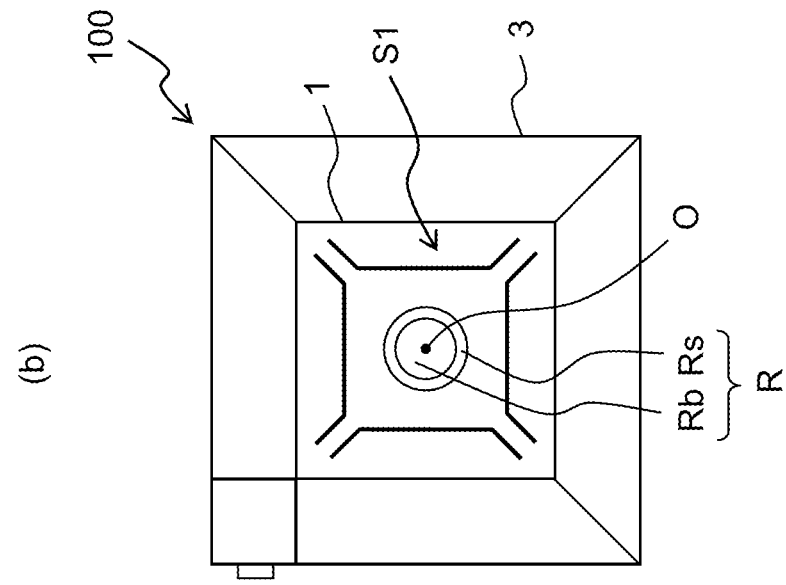
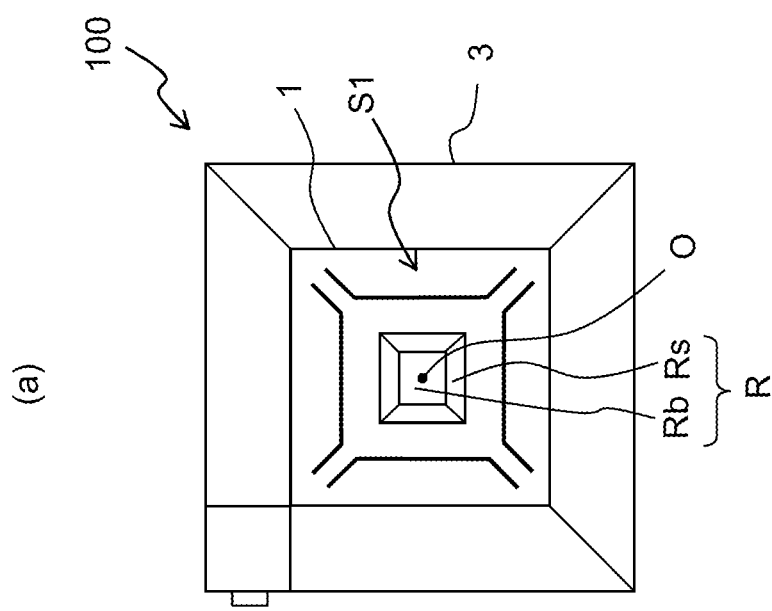
Fig. 9

Fig. 11
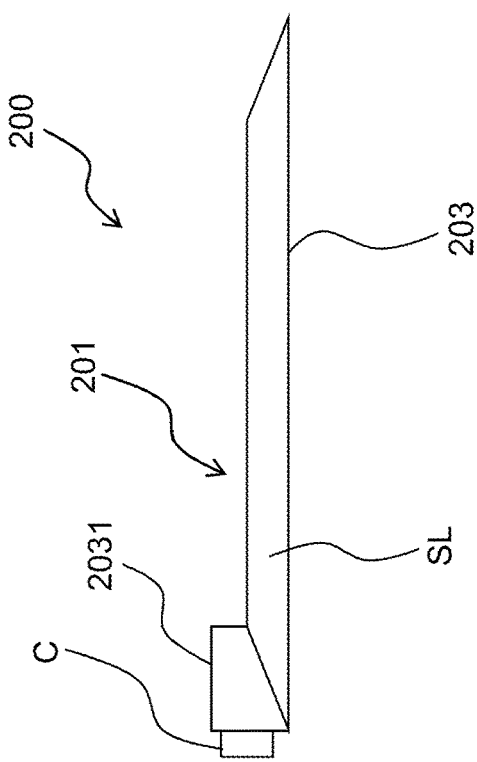
(b)
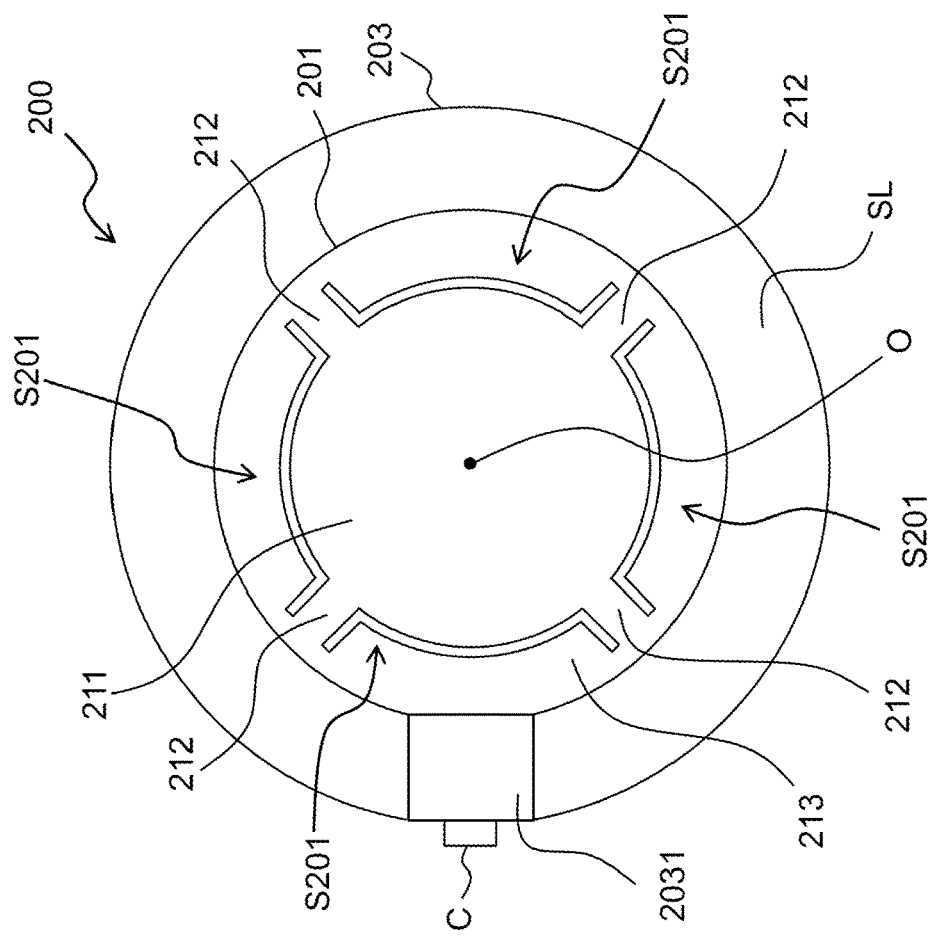
(a)

LOAD DETECTOR, METHOD FOR MANUFACTURING SAME, AND LOAD DETECTING SYSTEM

TECHNICAL FIELD

The present invention relates to a load detector, a method for manufacturing the load detector, and a load detecting system including the load detector.

BACKGROUND ART

In hospitals, nursing facilities, or the like, a load applied to a bed is detected to determine whether or not a patient or an inmate is present on the bed, and/or to obtain information such as a respiration rate of the patient or the like on the bed. A load detector for detecting load can be placed in various positions, for example under the support leg of the bed.

Patent Literature 1 discloses a load detector including a placing (mounting) plate part integrally formed with a cantilever portion and a slope adjoining the placing part.

Citation List

Patent Literature 1: Japanese Patent No. 5143946, specification.

SUMMARY

Technical Problem

Beds used in hospitals and/or nursing care facilities are typically provided with casters to assist in moving the bed. However, since the bed is heavy, it is difficult to say that the moving of the bed by using casters is easy, and in particular, it is physical labor and laborious work to place (mount) the caster provided on the leg of the bed on the placing plate part of the load detector such as disclosed in Patent Literature 1.

An object of the present invention is to provide a load detector capable of easily placing a caster of a bed on a placing part.

Solution to the Problem

According to a first aspect of the present invention, there is provided a load detector for detecting a load of a subject on a bed having a caster, the load detector including:

a plate portion which is one-fold and which is to be supported above an installation surface, on which the load detector is installed, separately from the installation surface; and a slope portion which is provided around the plate portion and which is inclined relative to a surface of the plate portion so as to extend between the surface of the plate portion and the installation surface, wherein the plate portion includes:
a peripheral part;
a placing part on which the caster is to be placed, and which is provided inside relative to the peripheral part separately from the peripheral part; and
a linking part which links the placing part and the peripheral part,
the load detector further comprising a strain sensor attached to the linking part,
wherein the slope portion includes at least two pairs of slopes each including a pair of slopes opposed to each other such that the placing part is interposed between the pair of slopes.

The load detector according to the first aspect may further include a reinforcing portion fixed to a lower surface of the placing part.

In the load detector according to the first aspect, the placing part may be separated from the peripheral part by a slit formed in the plate portion.

In the load detector according to the first aspect, the peripheral part may have a frame-shape surrounding the placing part.

In the load detector according to the first aspect, the strain sensor may be attached to a lower surface of the linking part.

In the load detector according to the first aspect, an upper surface of the placing part, an upper surface of the linking part, and an upper surface of the peripheral part may be flush with each other.

In the load detector according to the first aspect, a recess configured to restrict a movement of the caster may be provided in an upper surface of the placing part.

In the load detector according to the first aspect, an upper surface of the placing part may be a flat surface.

In the load detector according to the first aspect, the linking part may be a plurality of parts provided at equal intervals along a periphery of the placing part.

The load detector according to the first aspect may further include a guide member including the slope portion and a support portion configured to support the plate portion.

According to a second aspect of the present invention, there is provided a manufacturing method for the load detector according to the first aspect, the method including:

casting a member which is one-fold and which includes the plate portion and the slope portion;

cutting or grinding an area of the member corresponding to a lower surface of the linking part; and attaching the strain sensor to the area which has been cut or ground.

According to a third aspect of the present invention, there is provided a manufacturing method for the load detector according to the first aspect, the method including:

casting a member which is one-fold and which includes the plate portion and the reinforcing portion;

cutting or grinding an area of the member corresponding to a lower surface of the linking part; and attaching the strain sensor to the area which has been cut or ground.

According to a fourth aspect of the present invention, there is provided a load detecting system for detecting a load of a subject on a bed, the load detecting system comprising:

a plurality of load detectors; and a controller which is connected to the plurality of load detectors, and which is configured to obtain the load of the subject based on outputs of the plurality of load detectors, wherein each of the plurality of load detectors is the load detector according to the first aspect.

Effect of the Invention

According to the load detector of an aspect of the present invention, a caster of a bed can be easily placed on the placing part.

BRIEF DESCRIPTION OF THE DRAWINGS

FIG. 9(a) depicts an example of a recess that can be provided in the placing part, and FIG. 9(b) depicts another example of a recess that can be provided in the placing part.

FIG. 11(a) is a top view of a load detector of a modified example, and FIG. 11(b) is a side view of the load detector of the modified example.

DESCRIPTION OF EMBODIMENT

First Embodiment

Figure 6:
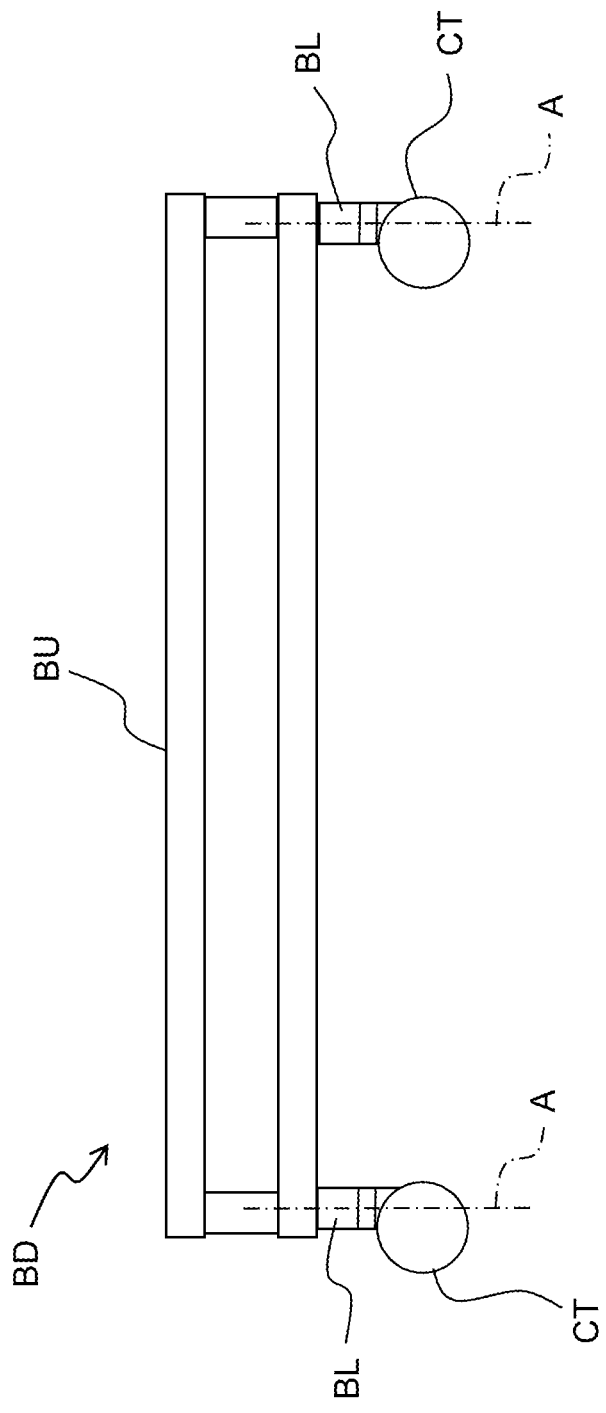
FIG. 6 depicts an example of a bed to be place on a load detector.

The load detector 100 of the first embodiment of the present invention will be described by exemplifying a situation in which a bed BD (FIG. 6) is placed (mounted) on the load detector 100 and a load of a subject on the bed BD is detected.

Figure 1:
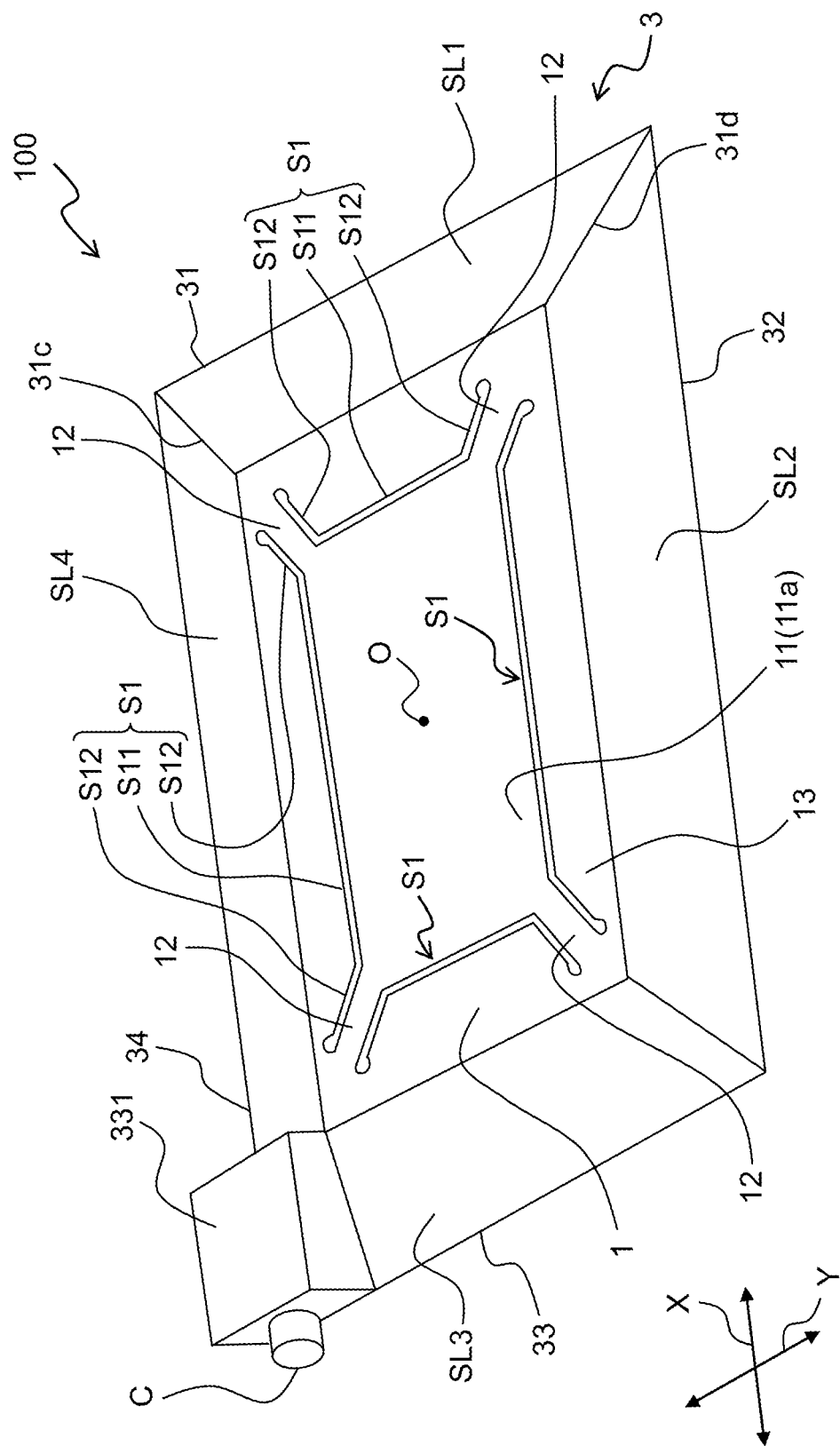
FIG. 1 is a perspective view of a load detector according to the first embodiment of the present invention.
Figure 2:
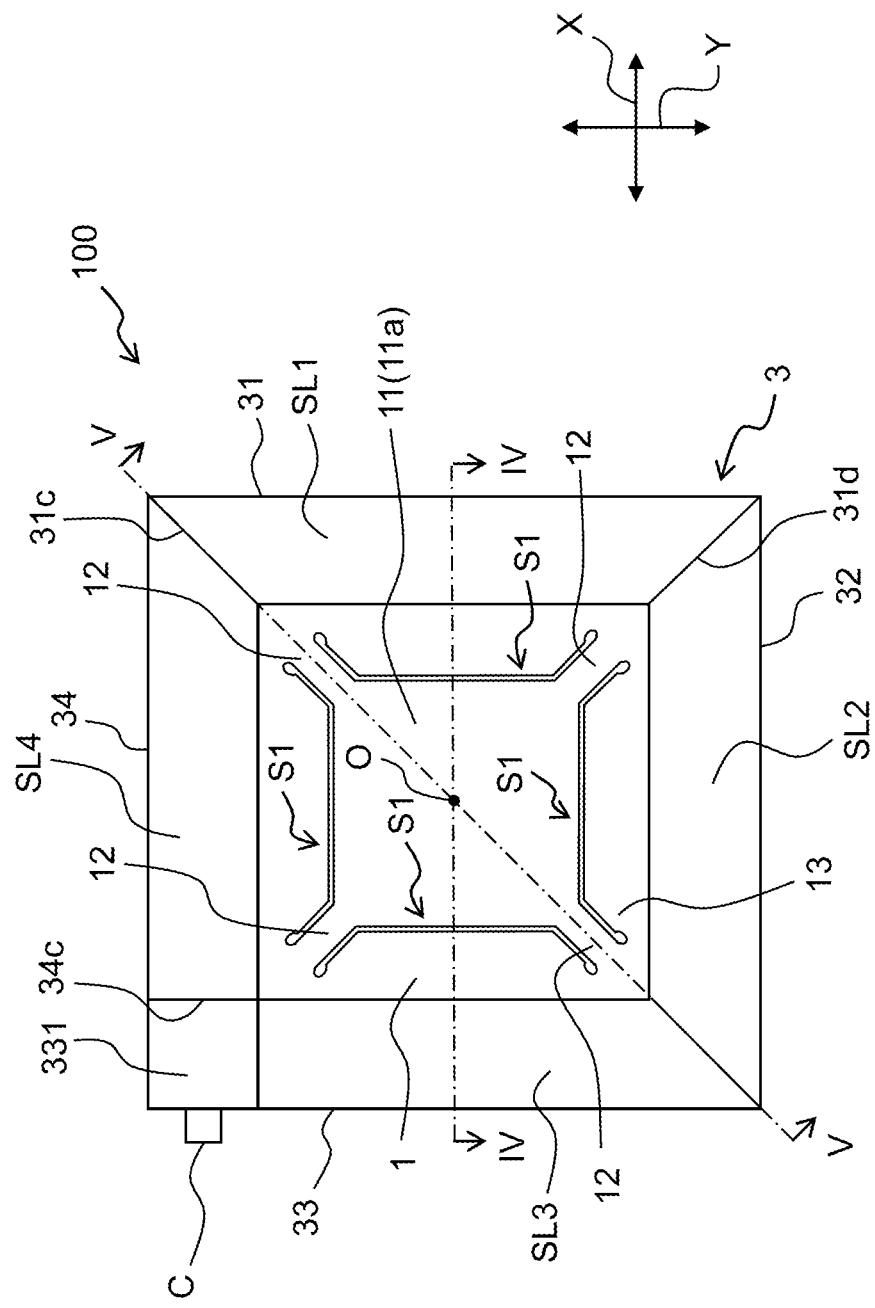
FIG. 2 is a top view of the load detector according to the first embodiment of the present invention.
Figure 3:
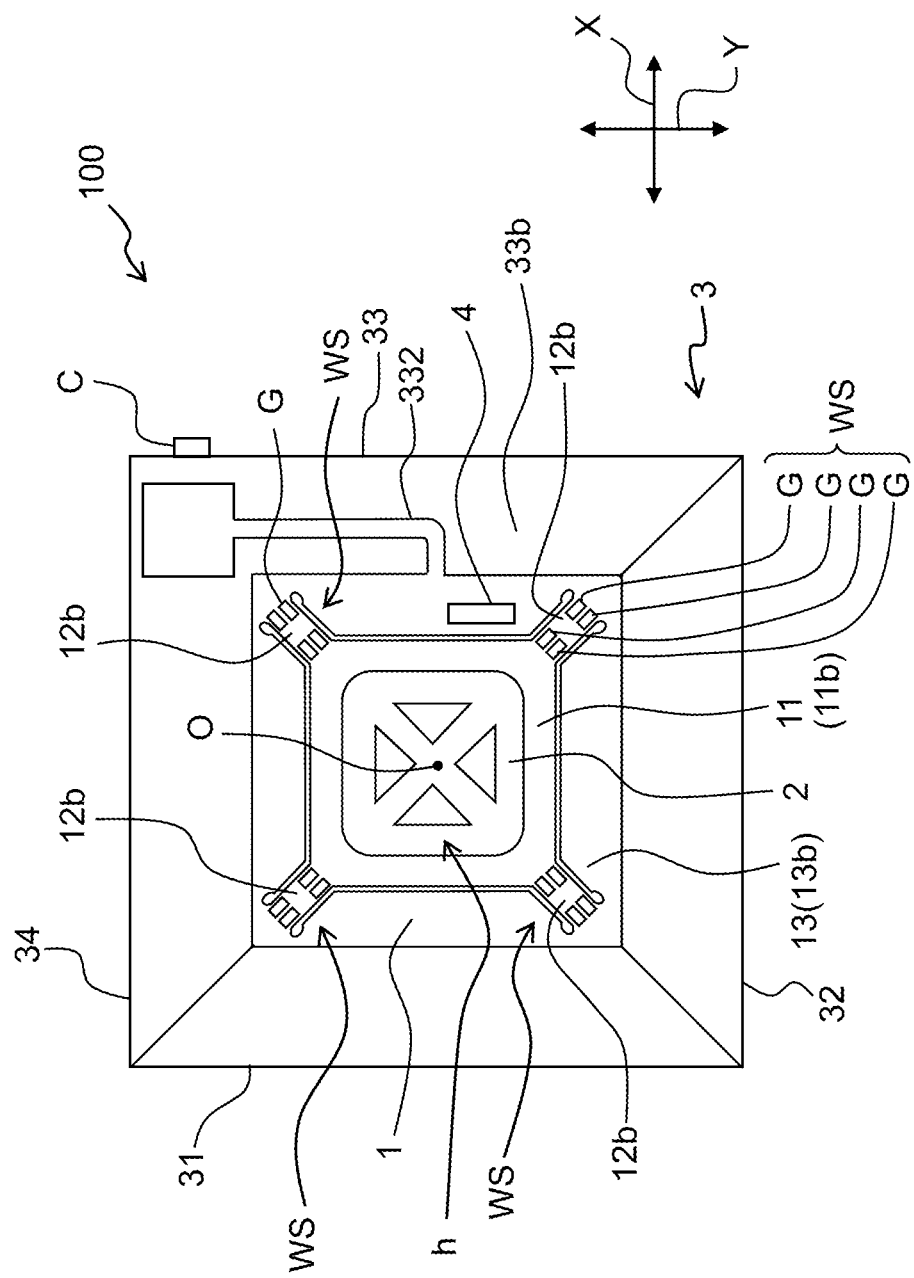
FIG. 3 is a bottom view of the load detector according to the first embodiment of the present invention.

As depicted in FIG. 1, FIG. 2, and FIG. 3, the load detector 100 mainly includes a plate portion 1 which is a square in plan view, and a guide portion 3 provided around the plate portion 1 and having a square frame shape in plan view. When using the load detector 100, the guide portion 3 is installed on the floor surface (installation surface) F (FIG. 4, FIG. 5), the plate portion 1 is supported by the guide portion 3 so that the plate portion 1 is arranged parallel to the floor F having a space between the plate portion 1 and the floor surface F. In a state that the load detector 100 is arranged on the floor F, the height of the upper surface of the plate portion 1 from the floor F may be about 5 mm to 15 mm as an example, but is not limited thereto.

In the following description, the center of the plate portion 1 is assumed to be the center O of the plate portion 1 and the load detector 100. A direction extending along one side of the plate portion 1 is defined as an X direction, and a direction extending along another side orthogonal to the one side of the plate portion 1 is defined as a Y direction. The surface facing away from the floor F in a state that the load detector 100 is installed on the floor F, is defined as the upper surfaces of the plate portion 1 and the guide portion 3, the surface facing toward the floor F in a state that the load detector 100 is installed on the floor F, is defined as the lower surfaces of the plate portion 1 and the guide portion 3.

The plate portion 1 is a one-fold (monolithic) flat plate extending in the same plane (within one plane). The plate portion 1 can be formed of stainless-steel (SUS304, etc.), but is not limited thereto. Plate portion 1 is divided, by four slits S1, into a placing part (placing area) 11, linking parts (linking areas, connecting parts) 12, and a peripheral part (peripheral area) 13. The upper surfaces of the placing part 11, the linking parts 12, and the peripheral part 13 are flush with each other.

Four slits S1 have the same shape to each other. One pair of the slits are provided on both sides in the X direction of the center O in line symmetrical about a straight line extending in the Y direction through the center O. The other pair of the slits are provided on both sides in the Y direction of the center O in line symmetrical about a straight line extending in the X direction through the center O. In other words, the four slits S1 are provided with four times (folds) rotational symmetry around the center O.

Each of the four slits S1 includes a first part S11 extending linearly in the side direction (X direction or Y direction) of the plate portion 1, and second parts S12 extending from both ends of the first part S11 away from the center O along the diagonal direction of the plate portion 1. The distal end portion of the second part S12 is rounded so as not to cause breakage in the plate portion 1 when the deflection occurs in the linking part 12.

The placing part 11 is a part (area), which is substantially square in plan view, defined at the center of the plate portion 1 by being separated (spaced) from the peripheral part 13 with the first parts S11 of the four slits S1. In this embodiment, the center of the placing part 11 matches the center O of the plate portion 1 and the load detector 100. When using the load detector 100, caster CT (FIG. 6) of the bed BD is placed on the upper surface 11a of the placing part 11.

On the lower surface 11b (FIG. 3) of the placing part 11, the reinforcing member (reinforcing portion) 2 is welded. The reinforcing member 2 is provided to prevent or suppress deflection that may occur in the placing part 11 when the caster CT is placed on the upper surface 11a of the placing part 11. In this embodiment, the reinforcing member 2 is a plate-like member that is adhered to the placing part 11 in parallel with the placing part 11 and has four substantially triangular cut-out portions h. However, the shape of the reinforcing member 2 is not limited thereto, and a member having various shapes such as a plate shape, a beam shape, or the like, which can prevent or suppress deflection that may occur in the placing part 11, can be used as the reinforcing member 2.

The linking part 12 is a part (area) linking (connecting) the placing part 11 and the peripheral part 13. Four linking parts 12 in total are defined at four corners of the placing part 11, respectively, with four slits S1.

Each of the linking parts 12 is an elongated part (area) defined by two opposing second parts S12 of two of the four slits S1 adjacent in circumferential direction around the center O. Each of the linking parts 12 extends along the diagonal direction of the plate portion 1 from the corner of the placing part 11 toward the peripheral part 13. In the longitudinal direction of the linking part 12, one end portion is continuous with the placing part 11, the other end portion is continuous with the peripheral part 13.

Four strain gages G are adhered (stuck) on a lower surface 12b of each of the linking parts 12. Two of the four strain gages G are adhered in the vicinity of one end portion in the longitudinal direction of the linking part 12 and remaining two of the four strain gages G are adhered in the vicinity of the other end portion in the longitudinal direction of the linking part 12. The distance between the two strain gages adhered in the vicinity of one end portion in the longitudinal direction of the linking part 12 and the center in the longitudinal direction of the linking part 12 is equal to the distance between the two strain gages adhered in the vicinity of the other end portion in the longitudinal direction of the linking part 12 and the center in the longitudinal direction of the linking part 12. Two strain gages G adhered in the vicinity of one end portion of the linking part 12 are arranged so that the distances from the lateral center of the linking part 12 are equal to each other, and two strain gages G adhered in the vicinity of the other end portion of the linking part 12 are arranged so that the distances from the lateral center of the linking part 12 are equal to each other. By adhering the strain gage G to the lower surface 12*b*, it is possible to prevent contact between the strain gage G and the caster CT or the like.

Four strain gages G each adhered to each of the linking parts 12 are connected to each other by a wiring (not depicted) to construct a Wheatstone bridge circuit WS.

The peripheral part 13 is a part (area) located outside of the four slits S1 with respect to the center O of the plate portion 1. The peripheral part 13 mainly guides the caster CT that have reached the plate portion 1 passing through the guide portion 3 to the placing part 11 smoothly.

In this embodiment, the peripheral part 13 is a part (area) having a frame shape surrounding the placing part 11 and four linking parts 12.

The guide portion 3 includes a first guide portion 31 and a third guide portion 33 provided on both sides of the plate portion 1 in the X direction, and includes the second guide portion 32 and a fourth guide portion 34 provided on both sides of the plate portion 1 in the Y direction.

The first guide portion 31 has a substantially triangular prism shape. One end surface 31*c* of the first guide portion 31 in the longitudinal direction is inclined 45° with respect to the longitudinal direction; and the other end surface 31*d* is inclined 45° with respect to the longitudinal direction and inclined 90° with respect to the end surface 31*c*. Therefore, the first guide portion 31 is trapezoidal in plan view (FIG. 2).

Figure 4:
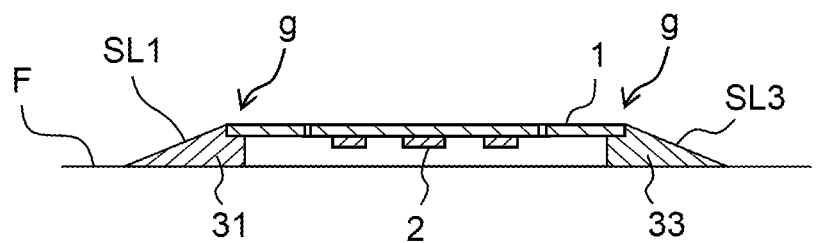
FIG. 4 is a cross-sectional view along line IV-IV of FIG. 2.
Figure 5:
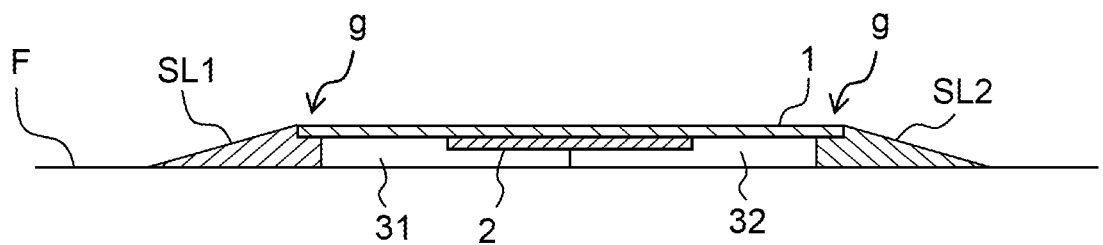
FIG. 5 is a cross-sectional view along line V-V of FIG. 2.

The cross section, of the first guide portion 31, orthogonal to the longitudinal direction thereof is substantially right-angled triangle (FIG. 4). The upper surface of the first guide portion 31 defining the oblique side in the cross section is a first slope SL1 for guiding the caster CT of the bed-BD onto the plate portion 1. Further, the upper end portion of the first slope SL1 is provided with a support groove g for supporting the plate portion 1.

The second guide portion 32 has the same shape as the first guide portion 31. The upper surface of the second guide portion 32 is a second slope SL2.

The third guide portion 33 has substantially the same shape as the first guide portion 31. The upper surface of the third guide portion 33 is a third slope SL3.

Meanwhile, unlike the first guide portion 31, a connector attaching portion 331 having a rectangular parallelepiped shape raised above the third slope SL3 is provided at one end of the third guide portion 33 in the longitudinal direction. A connector C for connecting the load detector 100 to a power supply and the data logger outside the load detector 100 is provided on the outer surface of the connector attaching portion 331.

Further, the wire accommodation channel 332 is provided (recessed) on the lower surface 33*b* (FIG. 3) of the third guide portion 33.

The fourth guide portion 34 has substantially the same shape as the first guide portion 31. The upper surface of the fourth guide portion 34 is a fourth slope SL4.

Meanwhile, unlike the first guide portion 31, the end surface 34*c* (FIG. 2) at one end of the fourth guide portion 34 in the longitudinal direction is orthogonal to the longitudinal direction.

The first guide portion 31, the second guide portion 32, the third guide portion 33, and the fourth guide portion 34 are arranged in this order, in the circumferential direction around the center O, so as to surround the plate portion 1. An edge of the plate portion at one side in the X-direction is disposed in the support groove g of the first guide portion 31 and fixed to the first guide portion 31 by a screw (not depicted). An edge of the plate portion at the other side in the X-direction is disposed in the support groove g of the third guide portion 33 and fixed to the third guide portion 33 by a screw (not depicted). Similarly, an edge of the plate portion 1 at one side in the Y-direction is disposed in the support groove g of the second guide portion 32 and fixed to the second guide portion 32 by a screw (not depicted); and an edge of the plate portion at the other side in the Y-direction is disposed in the support groove g of the fourth guide portion 34 and fixed to the fourth guide portion 34 by a screw (not depicted).

As depicted in FIG. 1 to FIG. 3, in a state that the first guide portion 31 to the fourth guide portion 34 are arranged around the plate portion 1, two ends of the first guide portion 31 to the fourth guide portion 34 facing each other are in close contact with each other such that the guide portion 3 having frame-shaped is formed.

A wiring for applying an input voltage to the Wheatstone bridge circuits WS, each constructed at each of the linking parts 12 of the plate portion 1, is provided below the plate portion 1. The wire connects the connector C and each of the Wheatstone bridge circuits WS through the wire accommodation channel 332.

On the lower surface 13*b* of the peripheral part 13 of the plate portion 1, there is provided a summing unit (summing circuit) 4 for summing the output of each of the Wheatstone bridge circuits WS, a wiring (not depicted) for connecting each of the Wheatstone bridge circuits WS and the summing unit 4, and a wiring (not depicted) for connecting the summing unit 4 and the connector C through the wire accommodation channel 332.

When performing load detection using the load detector 100, first, the caster CT of the bed BD is placed on the placing part 11 of the plate portion 1. Specifically, the caster CT is climbed onto the plate portion 1 through any of the slopes SL1 to SL4, and then placed on the placing part 11 via the peripheral part 13. The other three casters CT included in the bed BD are respectively placed on the other three load detectors 100.

The load of the subject on the bed BD is applied to the placing part 11 via the leg BL and the caster CT of the bed BD. With this, deflection occurs in each of the four linking parts 12 extending between the placing part 11 and the peripheral part 13 fixed to the guide portion 3 so as to change the resistance value in each of sixteen strain gages G adhered to the four linking parts 12.

The change in the resistance values of the sixteen strain gages G are output as changes in the output voltages of the four Wheatstone bridges WS. Then, the changes in the output voltages of the four Wheatstone bridges WS are summed in the summing unit 4, and the load of the subject S is obtained based on the obtained sum value.

The effects of the load detector 100 of the embodiment are summarized below.

The load detector 100 of the embodiment has slopes SL1, SL3 facing each other to sandwich the placing part 11, on which the caster CT of the bed BD is to be placed, in the X direction, and slopes SL2, SL4 facing each other to sandwich the placing part 11 in the Y direction. Therefore, the caster CT of the bed BD can be easily placed on the placing part 11 from substantially the entire area around the placing part 11 via at least one of the slopes SL to SL4.

Figure 7:
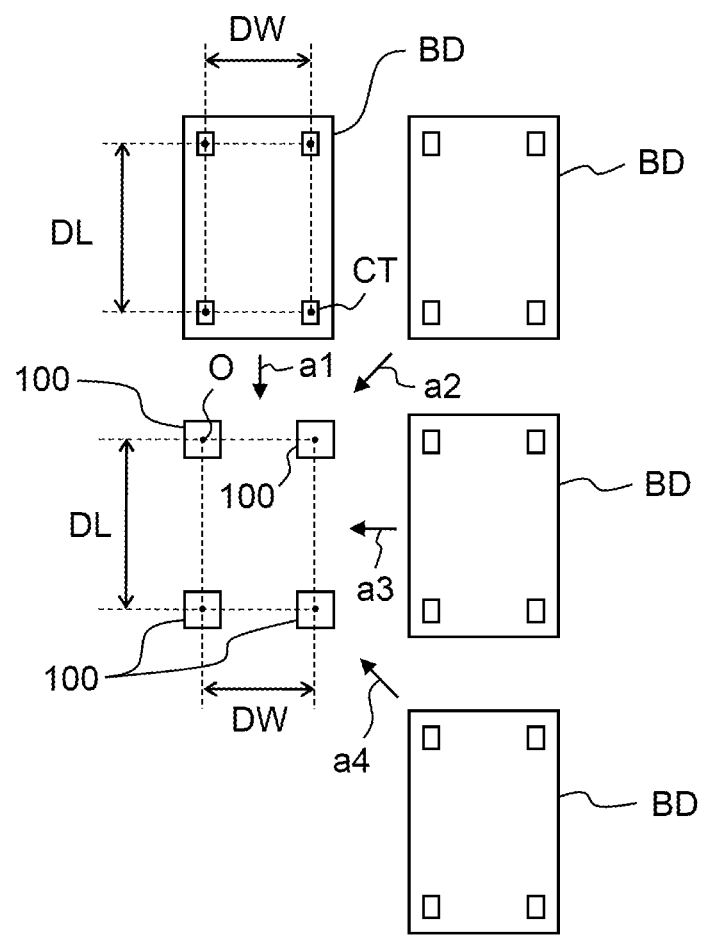
FIG. 7 is an illustrative view illustrating various aspects in which four casters of the bed are placed simultaneously on four load detectors.

For example, as depicted in FIG. 7, if four load detectors 100 are arranged on the floor in hospitals, nursing care facilities, or the like, so that the distance between the centers O of the load detectors 100 aligned in one direction matches the distance DL between the centers of the casters CT in the longitudinal direction of the bed BD, and the distance between the centers O of the load detectors 100 aligned in the direction orthogonal to the one direction matches the distance DW between the centers of the casters CT in the width direction of the bed BD, the four casters CT of the bed BD can be placed on the placing parts 11 of the four load detectors 100 simultaneously and quickly from various directions (see arrows a1, a2, a3, and a4 in FIG. 7).

This is particularly advantageous when a wall or a medical device exists around the bed BD, and a working space for placing the bed BD onto the load detector 100 cannot be sufficiently secured, or when an emergency patient or the like already exists on the bed BD, and the bed BD needs to be accurately placed onto the load detectors 100 without any delay.

Even when the work space and the work time for placing the bed onto the load detector can be sufficiently secured, it may be difficult for less experienced workers to move the bed linearly, in a predetermined direction limitedly required by the structure of the load detector, so as to place a plurality of casters onto a plurality of load detectors simultaneously and accurately. When the load detector 100 of the embodiment is used, a plurality of casters CT of the bed BD can be placed onto the placing parts 11 of a plurality of load detectors 100 simultaneously and accurately, even by less experienced workers, because various directions can be used to place the bed BD onto the load detector 100.

Further, in the load detector 100 of the embodiment, the slope SL1 to SL4 of the guide portion 3 is provided on substantially the entire area around the placing part 11 onto which the caster CT of the bed BD is placed, and thus the caster CT placed on the placing part 11 can be moved easily onto the floor F. When the direction for moving the caster CT from the placing part onto the floor surface is specified by the structure of the load detector in a limited manner, and the direction (traveling direction) of the caster CT on the placing part does not coincide with the specified direction, it is necessary to adjust the traveling direction of the caster CT by, for example, touching the caster CT directly by hand such that the travelling direction matches the specified direction, while the caster CT remains stationary on the placing part. However, since the load detector 100 of this embodiment can be moved from the placing part 11 to the floor F by moving the caster CT in various directions, there is no such trouble.

The load detector 100 of the embodiment has a structure as follows. That is, the plate portion 1 which has flat plate shape and in which the placing part 11, the linking parts 12, and the peripheral part 13 are formed is supported by the guide portion 3. Thus, the distance between the placing part 11 and the floor surface F (the height of the placing part 11) is small. Therefore, even when the bed BD is placed on the placing part 11, the distance between the upper surface BU (FIG. 6) of the bed BD and the floor surface F (the height of the upper surface BU) does not change greatly. Since the height of the upper surface BU of the bed BD is optimized in advance to a height suitable for performing a medical action and/or a care-giving action on a patient, a care-receiver, and the like on the bed, it is advantageous that the bed can be used without greatly changing the height of the upper surface BU. Further, since the distance between the placing part 11 and the floor surface F (the height of the placing part 11) is small, it does not require a large force to lift the caster CT onto the placing part 11 through the slope SL to SL4.

In the load detector 100 of the embodiment, the placing part 11 and the linking parts 12 are formed in the plate portion 1 having the flat plate shape, and thus, any wall portion or load cell or the like does not exist around the placing part 11. Therefore, even when any cover is provided for the caster CT of the bed BD or any medical device or wiring or the like is fixed to the leg BL of the bed BD, there is no fear that a part of the load detector 100 contacts such cover, device or the like. Thus, casters (beds) of various forms can be placed on the placing part 11 in a state that accurate load detection is capable.

In the load detector 100 of the embodiment, a reinforcing member 2 for preventing or suppressing the deflection of the plate portion 1 is provided on the lower surface of the placing part 11 of the plate portion 1. Thus, the amount of deflection occurring in the linking part 12 around the placing part 11 is optimized.

In the load detector 100 of the embodiment, a peripheral part 13, and a placing part 11 which is spaced from the peripheral part 13 by the slit S1 is formed in the plate portion 1 having the flat plate shape. Therefore, the caster CT having reached the plate portion 1 via any one of the slopes SL to SL4 can smoothly move onto the placing part 11 through the peripheral part 13 and the slit S1 without crossing any large gap that may impact the bed BD and/or a subject on the bed BD. Further, since the peripheral portion 13 has a frame shape surrounding the placing part 11, the caster CT can move smoothly onto the placing part 11 through the peripheral part 13 and the slit S1 in each of cases where the caster CT has reached the plate portion 1 via slopes SL1 to SL4.

Furthermore, in the load detector 100 of the embodiment, the placing part 11, the linking parts 12, and the peripheral part 13 are flush with each other, and thus, the caster CT having reached the peripheral part 13 can move smoothly onto the placing part 11.

Furthermore, in the load detector 100 of the embodiment, the upper surface of the plate portion 1 including the placing part 11 is a flat surface, and a wall portion or the like for stopping the caster CT by abutting the caster CT is not provided. Therefore, the caster CT having reached the placing part 11 is placed on the placing part 11 of the bed BD without causing a collision with the wall portion or the like that impacts the bed BD and/or a subject on the bed BD.

Such smooth movement and stop of the caster CT are particularly preferable in the case where an emergency patient, a care-receiver with weakness, or the like exists on the bed BD.

In the load detector 100 of the embodiment, the linking parts 12 are provided at the four corners of the rectangular placing part 11. Thus, it is possible to perform the load detection with high accuracy, by suppressing the effect of positional deviation error. The reason is as follows. That is, when a subject (caster CT) is placed at a position deviated from the center O of the plate portion 1, positional deviation error may occur in output of each of the Wheatstone bridges WS of four linking parts 12. However, by providing four linking parts 12 around the center O in rotational symmetry, the deviation error in each of the four Wheatstone bridges WS is canceled out in the sum of the outputs of the Wheatstone bridges WS of four linking parts 12.

Modified Examples

In the load detector 100 of the first embodiment, the following modifications can also be used.

The methods of providing the placing part 11, the linking part 12, and the peripheral part 13 in the plate portion 1 are not limited to the above-described aspect, and various aspects may be used.

Figure 8:
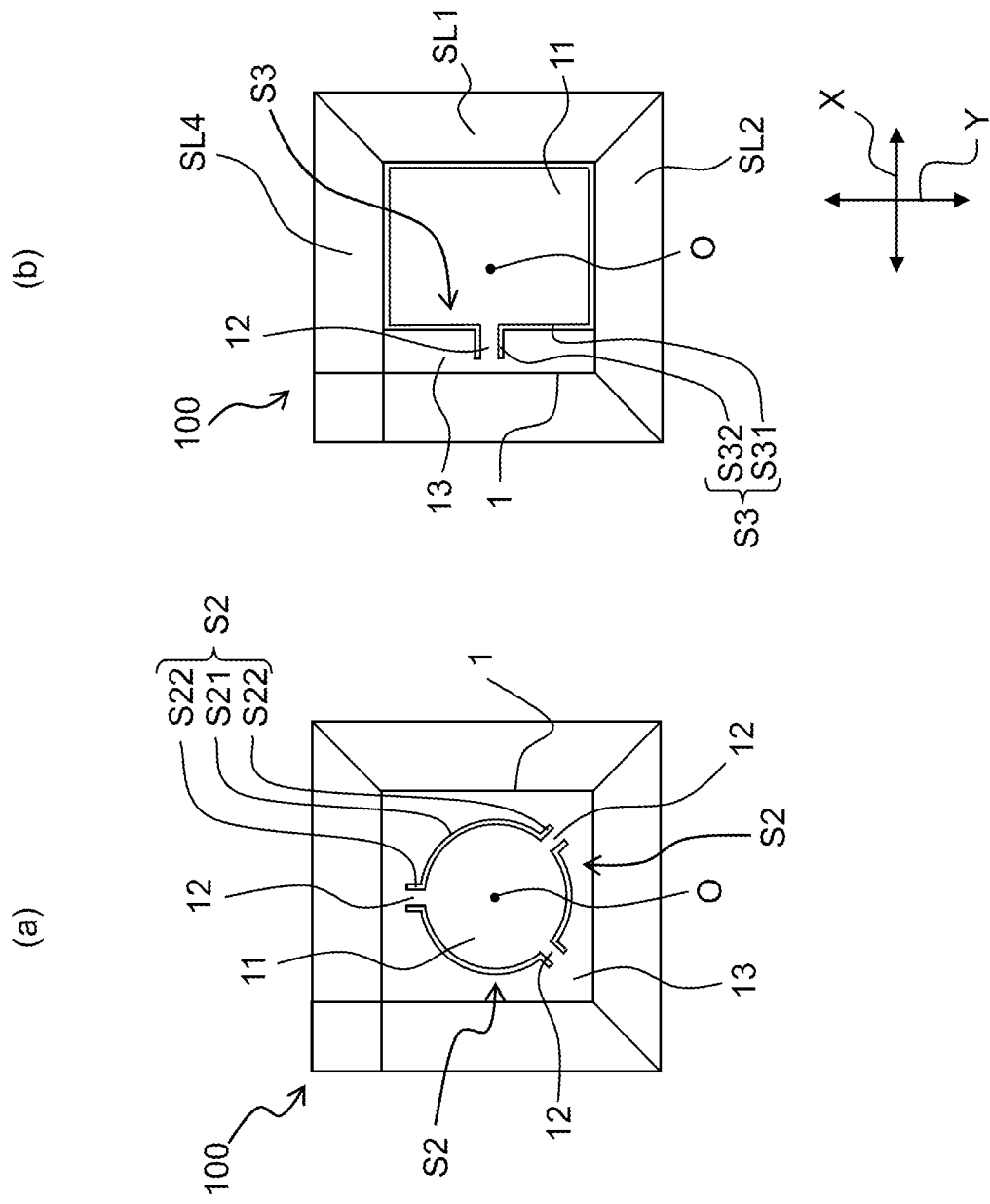
FIG. 8(a) depicts a plate portion of a modified example in which a placing part, a linking part, and a peripheral part are defined.
FIG. 8(b) depicts a plate portion of another modified example in which a placing part, a linking part, and a peripheral part are defined.

Specifically, for example, as depicted in FIG. 8(a), the slits S2 each including the arc-shaped first part S21, and the second portions S22 linearly extending from both ends of the first portion S21 may be formed so as to have three times (folds) rotational symmetry about the center O of the plate portion 1.

In this aspect, a substantially circular placing part 11 having the center O as the center is defined at the central portion of the plate portion 1 by the first parts S21 of the slits S2. Further three linking parts 12 each having an elongated shape are defined by second parts S22 of the slits S2 at three parts around the placing part 11 at equal intervals in the circumferential direction so as to extend from the placing part 11 in the radial direction of the placing part 11. In the plate portion 1, part other than the placing part 11 and the linking parts 12 is a peripheral part 13. Also, in this aspect, the placing part 11 is positioned inside relative to the peripheral part 13 having a frame shape, and is surrounded by the peripheral part 13. Further, the placing part 11 is separated from the peripheral part 13 by the slit S2.

In the plate portion 1 of the first embodiment and the modified examples, the number of linking parts 12 partitioned around the placing part 11 is not limited to four or three, and may be any number. Specifically, for example, the number of linking parts 12 may be eight or six. By arranging a plurality of linking parts 12 at equal intervals in the circumferential direction around the center O, like the plate portion 1 of the first embodiment, it is possible to achieve the effect of suppressing the effect of positional deviation error.

As depicted in FIG. 8(b), a pair of slits S3 each having substantially L-shape including a first part S31 extending linearly in the Y direction and a second portion S32 extending linearly in the X direction may be formed in line symmetry relative to a segment extending in the X direction through the center O.

In this aspect, the placing part 11 is defined in an area located on one side in the X-direction of the first portion S31 of the slit S3, and elongated linking part 12 is defined between the second portions S32 of the pair of slits S3. In the plate portion 1, a part other than the placing part 11 and the linking part 12 is a peripheral part 13. In this aspect, the part of the outer periphery of the placing part 11 facing the slope SL1, SL2, SL4 is configured such that it is separated from the slope SL1, SL2, SL4 with a gap. The caster CT introduced onto the placing part 11 via the slope SL1, SL2, or SL4 is placed on the placing part 11 without passing through the peripheral part 13.

In any of the plate portion 1 of the first embodiment and the plate portion 1 of the above modified examples, the placing part 11 is provided inside relative to the peripheral part 13 so as to be separated from the peripheral part. Here, "inside relative to the peripheral part" means a region within the plate portion located on the center side of the plate portion with respect to the peripheral part.

In the above first embodiment and the modified examples, the linking part 12 has an elongated shape, and specifically, is a rectangular shape. However, it is not limited thereto. The linking part 12 can be any shape as long as deflection occurs in the linking part 12 when the caster CT is placed on the placing part 11, and load can be detected via the strain gage G adhered to the linking part 12.

In the load detector 100 of the first embodiment, the upper surfaces of the placing part 11, the linking parts 12, and the peripheral part 13 of the plate portion 1 are flush with each other. However, it is not limited thereto. For example, the linking parts 12 may be inclined downward from the peripheral part 13 toward the placing part 11, and the upper surface of the placing part 11 may be placed lower position compared to the upper surface of the peripheral part 13. By doing so, the height of the placing part 11 from the floor surface is made smaller, and it is possible to further reduce the change in the height of the upper surface BU of the bed BD.

In the load detector 100 of the first embodiment, the upper surface 11a of the placing part 11 is a flat surface. However, it is not limited thereto. A recess (sunken part, concave part) R for restricting (regulating) move of the caster CT may be provided on the upper surface 11a of the placing part 11.

As depicted in FIG. 9(a), the recess R may be a recess of rectangular in plan view, having a flat bottom Rb of rectangular in plan view and slopes Rs extending from the bottom Rb on both sides in the X and Y directions. Alternatively, as depicted in FIG. 9(b), the recess R may be a recess of circular in plan view, having a flat bottom Rb of circular in plan view and slope Rs surrounding the bottom Rb. Other than the above, the recess R may be of any shape as long as the recess R can restrict move of the caster. In this modified example, the caster CT mounted on the placing part 11 is fitted into the recess R, and move of the caster CT is restricted. Note that, the center of the bottom Rb may coincide with the center O of the plate portion 1. In this case, move of the caster CT fitted into the recess R is restricted in a state that the caster CT is aligned with the center O of the plate portion 1 and thus more accurate measurement is possible.

In the load detector 100 of the first embodiment, the reinforcing member 2 for preventing or suppressing the deflection of the placing part 11 is fixed to the lower surface 11b of the placing part 11, but the reinforcing member 2 may be omitted.

In the load detector 100 of the first embodiment, the four-gage method in which four strain gages G are adhered to each of the linking parts 12 of the plate portion 1 to construct the Wheatstone bridge WS is applied. However, it is not limited thereto. For example, the one-gage method or two-gage method may be used to adhere one or two strain gage(s) to the linking part 12. Instead of the strain gage(s), any strain detector capable of detecting strain occurred in the linking part 12 can be used. These are collectively referred to as strain sensor(s).

Figure 10:
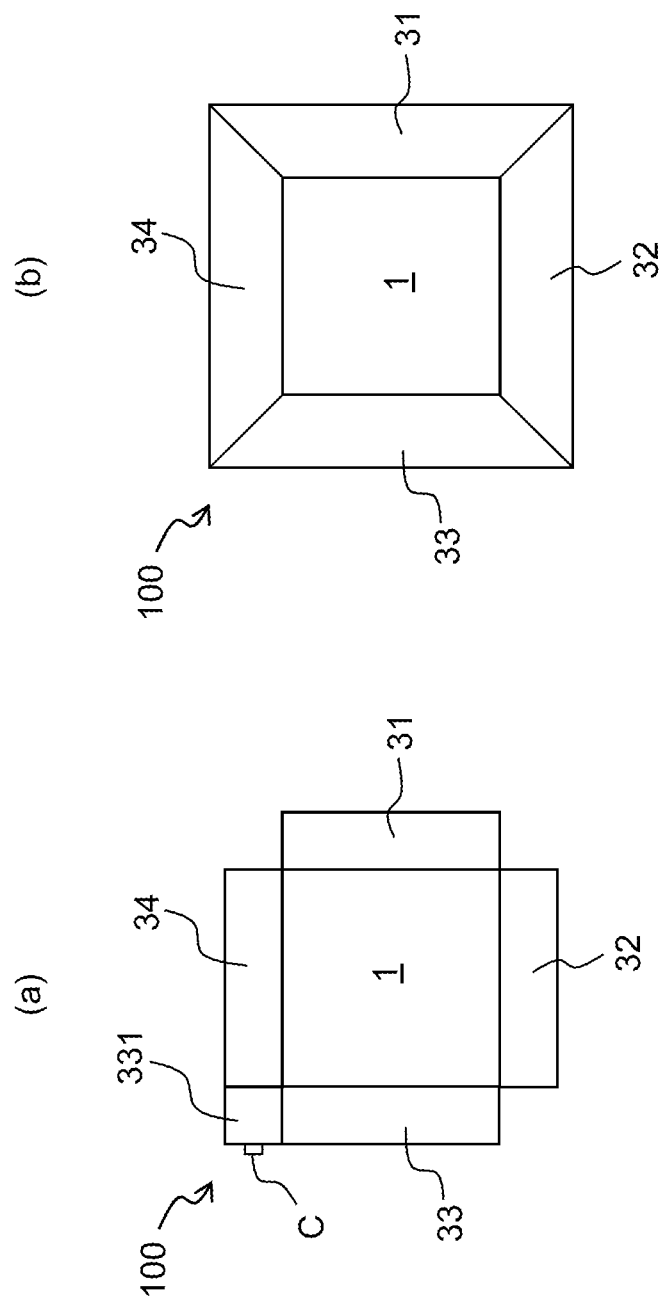
FIG. 10(a) is a plan view depicting a modified example of a guide portion.
FIG. 10(b) is a plan view depicting another modified example of the guide portion.

In the load detector 100 of the first embodiment, one of the slopes SL1 to SL4 of the guide portion 3 is provided on substantially the entire area, of the periphery of the plate portion 1, except for the portion where the connector attaching portion 331 is provided. However, it is not limited thereto. Specifically, for example, as depicted in FIG. 10(a), the load detector may be configured such that no slope is formed in the vicinities of corners of the plate portion 1 by allowing each of the first guide portion 31 to fourth guide portion 34 to have end surfaces in the longitudinal direction orthogonal to the longitudinal direction. Even with such an aspect, the caster CT can be easily mounted on the placing part 11 from both sides in the X direction and both sides in the Y direction of the placing part 11.

Alternatively, as depicted in FIG. 10(b), the load detector may be configured such that slopes are formed in the entire area around the placing part 11, by making the third guide portion 33 and the fourth guide portion 34 have the same shape as the first guide portion 31. In this aspect without the connector attaching portion 331 and the connector C, power supply to the load detector 100 and output extraction may be achieved wirelessly, for example. Alternatively, power supply to the load detector 100 and output extraction may be achieved via a wiring extending downwardly from the load detector 100 and inside the floor F.

In the load detector 100 of the first embodiment, the guide portion 3 including the slopes SL1 to SL4 supports the plate portion 1 (i.e., a support portion for supporting the plate portion, and the slope is formed as an integral guide portion). However, it is not limited thereto. The support portion supporting the plate portion 1 and the slope for guiding the caster CT to the plate portion 1 may be separate members. Specifically, for example, as well as supporting the outer periphery of the plate portion 1 by placing the lower surface of the plate portion 1 on the frame-shaped support portion of square in plan view, plate-shaped slopes separated from the frame-shaped support portion may be attached to the upper surface of the plate portion 1 at four sides of the plate portion 1 so as to construct the slopes for guiding the caster CT on the floor F to the placing part 11. Alternatively, the slope itself may be a support for supporting the plate portion. Specifically, for example, the upper end of the plate-shaped slope is fixed to the outer periphery of the plate portion 1 so as to support the plate portion 1 by the slope.

In the load detector 100 of the first embodiment, the plan view shape of the plate portion 1 is square, the plan view shape of the guide portion 3 is a square frame shape. However, it is not limited thereto. The plan view shape of the plate portion 1 may be a rectangular, and the plan view shape of the guide portion 3 may be a rectangular frame shape.

Alternatively, like the load detector 200 of the modified example depicted in FIG. 11(a) and FIG. 11(b), a configuration including a plate portion 201 of circular in plan view, and a guide portion 203 of annular in plan view can be adopted.

The plate portion 201 is divided into circular placing part 211, four linking parts 212 of an elongated shape, and substantially annular peripheral portion 213 by four slits S201 provided in four times rotational symmetry about the center O of the plate portion 201. On the upper surface of the guide portion 203, a slope SL located in substantially entire area in circumferential direction of the plate portion 201 and a connector attaching portion 2031 formed at a position where there is no slope SL is formed. The connector C is attached to the connector attaching portion 2031.

Note that, even in an aspect where a continuous slope SL of substantially annular in plan view is formed around the circular plate portion 201 like this modified example, the slopes SL exist on both sides of the plate portion 201 in each of two radial directions perpendicular to each other, and thus it can be regarded that at least two pairs of slopes are provided on both sides in the X direction and on both sides in the Y direction of the plate portion 201.

The load detectors of the first embodiment and the modified examples can also be used to detect load of a subject on a stretcher or a delivery table. In the present invention, "bed" includes equipment, other than bed, which is used in medical facilities and/or nursing facilities and which is configured such that a patient and/or a care-receiver lies on the equipment, such as a stretcher, a delivery table, and the like.

Manufacturing Method

Next, a manufacturing method of the load detector 100 of the first embodiment will be explained.

In the manufacture of the load detector 100, first, a plate portion 1 is obtained by cutting a plate material of stainless steel in a square shape. Then, four slits S1 is formed in the plate portion 1 to define the placing part 11, the linking parts 12, and the peripheral part 13 in the plate portion 1. Further, the first guide member 31 to the fourth guide member 34 for constructing the guide portion 3 is prepared by casting or the like.

Then, the reinforcing member 2 is fixed to the lower surface 11b of the placing part 11 by welding, and four strain gages G are adhered to the lower surface 12b of each of four linking parts 12. In this case, the strain gage unit in which four strain gages G are arranged on one sheet at a predetermined positional relationship may be used.

Then, the outer peripheral portion of the plate portion 1 is disposed in the support grooves g of the first guide portion 31 to the fourth guide portion 34, and the plate portion 1 is fixed to the first guide portion 31 to the fourth guide portion 34 by fasteners such as screws.

Finally, in each of the four linking parts 12, four strain gages are connected by wiring to construct the Wheatstone bridge WG, the summing unit 4 and the connector C is provided on the load detector 100, and wiring for connecting them is applied.

Note that, a structure corresponding to the plate portion 1 having four slits S1 and the reinforcing member 2 fixed to the placing part 11 may be integrally molded by casting. In this case, after the structure is obtained by casting, regions (areas) corresponding to the back surfaces 12b of the four linking parts 12 in the structure are cut or ground to reduce the surface roughness of the regions and to adjust the thickness of the linking parts 12. Those are performed for adhering the strain gages G to the linking parts 12 satisfactorily, and for increasing measurement accuracy of the load detector 100 by making thicknesses of the four linking parts 12 equal to each other.

Thereafter, adhering of the strain gages G to the linking parts 12, fixing of the plate portion 1 to the first guide portion 31 to the fourth guide portion 34 by processes similar to the above, applying of wiring, and the like are performed to obtain the load detector 100.

Other than the above, a structure corresponding to the plate portion 1 having four slits S and the guide portion 3 may be integrally formed by casting. Again, after the structure is obtained by casting, regions corresponding to the back surfaces 12b of the four linking parts 12 in the structure are cut or ground to reduce the surface roughness of the regions and to adjust the thickness of the linking parts 12. Note that, the integral molding (solid casting) may be performed while further including a structure corresponding to the reinforcing member 2.

Thereafter, adhering of the strain gages G to the linking parts 12, applying of wiring and the like are performed to obtain a load detector 100.

Second Embodiment

Figure 12:
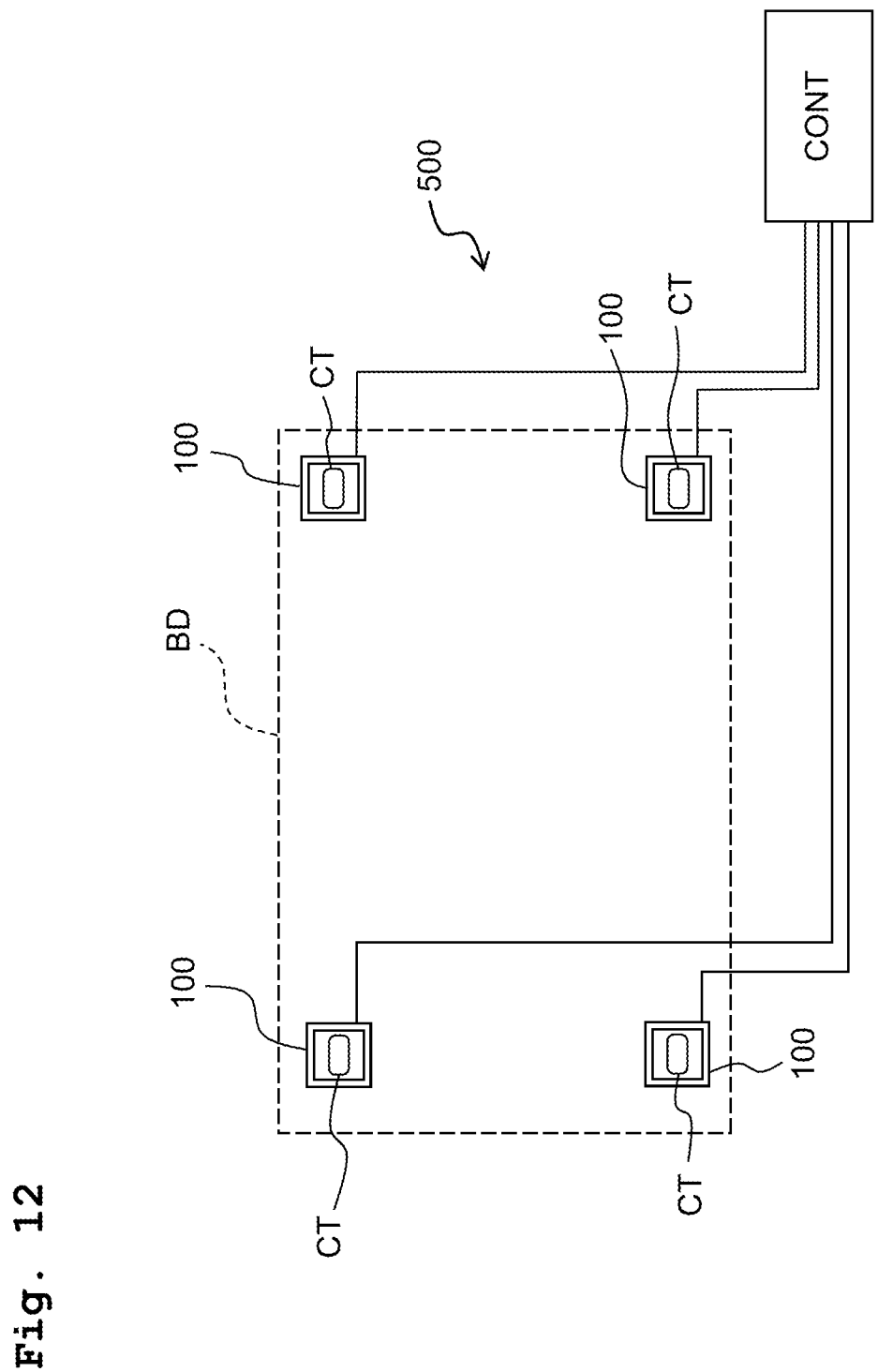
FIG. 12 is a schematic view depicting a configuration of a load detecting system according to a second embodiment of the present invention.

The load detecting systems 500 of the second embodiment will be explained with reference to FIG. 12.

The load detecting system 500 mainly includes four load detectors 100 and a controller CONT. The four load detectors 100 and the controller CONT are connected by wiring.

When using the load detecting system 500, the four load detectors 100 are arranged on the floor F with a positional relationship corresponding to the four casters CT of the bed BD (FIG. 7). The bed BD is then moved in any direction to place the bed BD on the four load detectors 100 via any one of the slopes SL1 to SL4. By doing so, each of the four load detectors 100 detects a portion of the load of the subject on the bed BD applied via the leg BL of the bed BD.

A controller CONT connected to the four load detectors 100 sums the outputs from the four load detectors 100 to obtain the load value of the subject on the bed BD.

Since the load detecting system 500 of the embodiment uses the load detector 100 of the first embodiment, it is possible to obtain the same effect as the load detector 100 of the first embodiment. In particular, the four casters CT of the bed BD can be placed on the placing parts 11 of the four load detectors 100 simultaneously and quickly from various directions.

The present invention is not limited to the embodiment described above provided that the feature of the present invention is maintained. Other embodiments, which are conceivable within the scope of the technical concept of the present invention, are also included in the scope of the present invention.

INDUSTRIAL APPLICABILITY

According to the load detector of the present invention, casters of beds can be easily placed on a placing part. Therefore, when the load detector is used in hospitals, nursing facilities, or the like, it is possible to easily and accurately arrange the bed on the load detector even in a situation where there is no space margin or time margin, thereby contributing to improvement in the quality of medical care or nursing care.

PARTS LIST

1, 201 plate portion; 2 reinforcing member; 3, 203 guide member; 4 summing unit; 11, 211 placing part; 12, 212 linking part; 13, 213 peripheral part; 31 first guide portion; 32 second guide portion; 33 third guide portion; 34 fourth guide portion; 100, 200 load detector; 331, 2031 connector attaching portion; 500 load detecting system; BD bed; CT caster; S, S2, S3, S201 slit; SL1, SL2, SL3, SL4, SL slope; R recess (sunken part, concave part)

The invention claimed is:

1. A load detector for detecting a load of a subject on a bed having a caster, the load detector comprising:
   a plate portion which is one-fold and which is to be supported above an installation surface, on which the load detector is installed, separately from the installation surface; and
   a slope portion which is provided around the plate portion and which is inclined relative to a surface of the plate portion so as to extend between the surface of the plate portion and the installation surface, wherein
   the plate portion includes:
      a peripheral part;
      a placing part on which the caster is to be placed, and which is provided inside relative to the peripheral part separately from the peripheral part; and
      a linking part which links the placing part and the peripheral part,
   the load detector further comprising a strain sensor attached to the linking part,
   wherein the slope portion includes first and second slopes opposed to each other in a first direction such that the plate portion is interposed between the first and second slopes, and third and fourth slopes opposed to each other in a second direction orthogonal to the first direction such that the plate portion is interposed between the third and fourth slopes,
   the first slope is raised from the installation surface to the plate portion along the first direction such that the caster is guided from the installation surface to the plate portion through an upper surface of the first slope,
   the second slope is raised from the installation surface to the plate portion along the first direction such that the caster is guided from the installation surface to the plate portion through an upper surface of the second slope,
   the third slope is raised from the installation surface to the plate portion along the second direction such that the caster is guided from the installation surface to the plate portion through an upper surface of the third slope,
   the fourth slope is raised from the installation surface to the plate portion along the second direction such that the caster is guided from the installation surface to the plate portion through an upper surface of the fourth slope, and
   the linking part is a plurality of parts each having a diagonal orientation extending from respective corners of the placing part toward the peripheral part.

2. The load detector according to claim 1, further comprising a reinforcing portion fixed to a lower surface of the placing part.

3. The load detector according to claim 1, wherein the placing part is separated from the peripheral part by a slit formed in the plate portion.

4. The load detector according to claim 1, wherein the peripheral part has a frame-shape surrounding the placing part.

5. The load detector according to claim 1, wherein the strain sensor is attached to a lower surface of the linking part.

6. The load detector according to claim 1, wherein an upper surface of the placing part, an upper surface of the linking part, and an upper surface of the peripheral part are flush with each other.

7. The load detector according to claim 1, wherein a recess configured to restrict a movement of the caster is provided in an upper surface of the placing part.

8. The load detector according to claim 1, wherein an upper surface of the placing part is a flat surface.

9. The load detector according to claim 1, wherein the plurality of parts of the linking part is provided at equal intervals along a periphery of the placing part.

10. The load detector according to claim 1, further comprising a guide member including the slope portion and a support portion configured to support the plate portion.

11. A manufacturing method for the load detector as defined in claim 1, the method comprising:
   casting a member which is one-fold and which includes the plate portion and the slope portion;
   cutting or grinding an area of the member corresponding to a lower surface of the linking part; and
   attaching the strain sensor to the area which has been cut or ground.

12. A manufacturing method for the load detector as defined in claim 2, the method comprising:
   casting a member which is one-fold and which includes the plate portion and the reinforcing portion;
   cutting or grinding an area of the member corresponding to a lower surface of the linking part; and
   attaching the strain sensor to the area which has been cut or ground.

13. A load detecting system for detecting a load of a subject on a bed, the load detecting system comprising:
   a plurality of load detectors; and a controller which is connected to the plurality of load detectors, and which is configured to obtain the load of the subject based on outputs of the plurality of load detectors, wherein each of the plurality of load detectors is the load detector as defined in claim 1.

14. A load detector for detecting a load of a subject on a bed having a caster, the load detector comprising:

a plate portion which is one-fold and which is to be supported above an installation surface, on which the load detector is installed, separately from the installation surface; and a slope portion which is provided around the plate portion and which is inclined relative to a surface of the plate portion so as to extend between the surface of the plate portion and the installation surface, wherein the plate portion includes:

a peripheral part;

a placing part on which the caster is to be placed, and which is provided inside relative to the peripheral part separately from the peripheral part; and a linking part which links the placing part and the peripheral part, the load detector further comprising a strain sensor attached to the linking part, wherein the slope portion includes at least two pairs of slopes each including a pair of slopes opposed to each other such that the placing part is interposed between the pair of slopes, a plurality of slits is formed in the plate portion such that the placing part is separated from the peripheral part by the plurality of slits and the linking part is interposed between two slits of the plurality of slits, the peripheral part has a frame-shape surrounding a whole circumference of the placing part, and the plurality of slits extends around the circumference of the placing part, and the linking part is a plurality of parts each having a diagonal orientation extending from respective corners of the placing part toward the peripheral part.

15. A load detector for detecting a load of a subject on a bed having a caster, the load detector comprising:

a plate portion which is one-fold and which is to be supported above an installation surface, on which the load detector is installed, separately from the installation surface; and a slope portion which is provided around the plate portion and which is inclined relative to a surface of the plate portion so as to extend between the surface of the plate portion and the installation surface, wherein the plate portion is divided by a plurality of slits into:

a peripheral part;

a placing part on which the caster is to be placed, and which is provided inside relative to the peripheral part separately from the peripheral part; and a linking part which links the placing part and the peripheral part, the load detector further comprising a strain sensor attached to the linking part, wherein the slope portion includes at least two pairs of slopes each including a pair of slopes opposed to each other such that the placing part is interposed between the pair of slopes, the plurality of slits is formed in the plate portion such that the placing part is separated from the peripheral part by the plurality of slits and the linking part is interposed between two slits of the plurality of slits, and the linking part is a plurality of parts each having a diagonal orientation extending from respective corners of the placing part toward the peripheral part.

* * * * *